United States Patent
Jacobsen et al.

(10) Patent No.: US 6,183,410 B1
(45) Date of Patent: Feb. 6, 2001

(54) RADIATION EXPOSURE DEVICE FOR BLOOD VESSELS, BODY CAVITIES AND THE LIKE

(75) Inventors: Stephen C. Jacobsen, Salt Lake City; John Lippert, Park City; Kent Backman; Clark C. Davis, both of Salt Lake City, all of UT (US)

(73) Assignee: Precision Vascular Systems, Inc., Salt Lake City, UT (US)

( * ) Notice: Under 35 U.S.C. 154(b), the term of this patent shall be extended for 0 days.

(21) Appl. No.: 09/306,079

(22) Filed: May 6, 1999

(51) Int. Cl.$^7$ ........................................ A61N 5/00
(52) U.S. Cl. ................................................ 600/3
(58) Field of Search ................... 600/3, 4, 5, 7; 604/500, 516, 528

(56) References Cited

U.S. PATENT DOCUMENTS

| | | | |
|---|---|---|---|
| 4,957,476 | * | 9/1990 | Cano ........................................ 600/3 |
| 5,976,106 | * | 11/1999 | Verin et al. .............................. 600/3 |
| 6,053,900 | * | 4/2000 | Brown et al. ........................ 604/500 |

* cited by examiner

*Primary Examiner*—Max Hindenburg
*Assistant Examiner*—Brian Szmal
(74) *Attorney, Agent, or Firm*—Thorpe, North & Western, LLP

(57) ABSTRACT

A device and method for irradiating with a desired radioactive emission the interior walls of blood vessels, body cavities and the like. The device includes a catheter for placement in the blood vessel, body cavity or the like, adapted for disposition adjacent the walls thereof. The distal end of the catheter is preferably configured to expand into a helical coil shape when unconstrained, but may be straightened when constrained within a second catheter. The catheter includes a section which is opaque to the radioactive emissions in question, and a wire slidably disposed therein for threading selectable distances into the catheter. A radioactive source is positioned at the distal end of the wire, and when positioned within the radio-opaque section of the catheter, radioactive emissions arc blocked from reaching adjacent tissue, allowing the radiation source to be safely guided to a target location. Upon reaching the target location, the radioactive source is moved out of the opaque section, and radioactive emissions are allowed to reach adjacent tissue for treatment. The radiation source is preferably retracted through the catheter at a variable rate, so as to vary the radiation exposure level of adjacent tissues.

40 Claims, 4 Drawing Sheets

RADIATION EXPOSURE DEVICE FOR BLOOD VESSELS, BODY CAVITIES AND THE LIKE

BACKGROUND OF THE INVENTION

1. Field of the Invention

This invention relates to a device which may be inserted into blood vessels, body cavities, etc. for radiating selectable areas in the vessels or cavities, for therapeutic or other purposes. More particularly, the present invention relates to an expandable catheter for placing in direct contact with a selected area in a blood vessel, body cavity or the like, which allows both radial and longitudinal control of radiation dosage.

2. State of the Art

Catheters have long been used for threading into blood vessels or other body orifices for such purposes as delivering emboli to target locations, delivering therapeutic drugs to such locations, sensing conditions in the vessel or cavity by sensors inserted into the catheter, etc. Typically, a guide wire is first threaded into the vessel or cavity until the distal end of the guide wire reaches a target location, and then the catheter which is placed about the guide wire is moved to the target location as guided by the guide wire. Then, depending upon the treatment, the guide wire may be withdrawn or left in place and the treatment commenced, such as by injecting drugs through the catheter to the target location.

There are some diseases, such as restenosis, which become sited in blood vessels or body cavities which cannot be effectively treated by drugs, but instead respond to appropriate doses of radiation from a radioactive source. Effective treatment of such diseases requires exposure of diseased tissues to levels of radiation within a therapeutic range. This presents a problem if the diseased areas are not readily accessible but can only be reached by a pathway which extends past healthy tissue to the diseased area. It would thus be desirable to have an apparatus for selectively exposing areas of blood vessels, body cavities and the like to radiation from a radioactive source which may be threaded into a patient's anatomy such as by means of a catheter.

However, it is desirable to provide the radiation dose to the diseased area without exposing surrounding healthy tissue to such radiation. Thus, it is desirable to place the radiation source in as close a proximity to the diseased area as possible in order to produce a desired benefit, while also keeping the radiation source as far away from healthy tissue as possible. It would thus be desirable to provide an apparatus and method for selectively exposing areas of blood vessels, body cavities and the like to radiation in which healthy tissue in such vessels and cavities are protected from such radiation during insertion of the device and treatment therewith. It would thus also be desirable to have an apparatus for selectively exposing areas of blood vessels, body cavities and the like to radiation from a radioactive source wherein the radiation dose may be both radially and longitudinally controlled relative to the patient's anatomy.

OBJECTS AND SUMMARY OF THE INVENTION

It is therefore an object of the invention to provide a method and apparatus for selectively exposing areas of blood vessels, body cavities and the like to radiation from a radioactive source inside.

It is another object of the invention to provide such an apparatus which allows sufficient flow of bodily fluids around or through the apparatus during insertion and treatment.

It is still another object of the invention to provide an apparatus for selectively exposing areas of blood vessels, body cavities and the like to radiation from a radioactive source wherein the radiation dose may be both radially and longitudinally controlled relative to the patient's anatomy.

It is also an object of the invention to provide such an apparatus and method in which healthy tissue in such vessels and cavities are protected from radiation during treatment.

It is yet another object of the invention to provide such an apparatus and method which allows for the safe handling and insertion of the radiation source into blood vessels, body cavities and the like.

It is a further object of the invention, in accordance with one aspect thereof, to provide such a method and apparatus which allows for selectively placing a radiation source in close proximity to a target area, but removed from adjacent areas.

The above and other objects of the invention are realized in a specific illustrative embodiment of apparatus for selectively irradiating blood vessels, body cavities and the like. Such apparatus includes a catheter having a distal end for threading into a blood vessel or body cavity, and having at least one lumen. Also included is a wire for threading into the lumen of the catheter, the wire having a proximal end and a distal end, and a radiation source disposed near the distal end for irradiating tissue adjacent to the radiation source.

In accordance with one aspect of the invention, the catheter includes a section which absorbs radiation from the radiation source so that when the radiation source is positioned within the section, radiation is substantially blocked or reduced from reaching adjacent tissue.

In accordance with another aspect of the invention, a portion of the catheter near the distal end is formed to spread apart when positioned in a blood vessel or cavity, and move into close proximity or contact with the vessel or cavity walls where a diseased area is located. Then, the radiation source on the wire may be moved in the catheter to a position adjacent the diseased area, for irradiating the diseased area.

In use, the wire would be threaded into the lumen of the catheter until the radiation source is positioned within the section which is absorbent of radiation, and then the catheter and wire would be threaded either directly into the blood vessel or cavity, or through another larger catheter to the target area in the vessel or cavity. All the time during the movement of the catheter to the target location, the radiation source would be maintained within the absorbent section of the catheter to reduce the chance of radiation damage to healthy tissue past which the radiation source is moved.

After the end portion of the catheter has moved to the target location, the wire is manipulated so that the radiation source is moved out of the absorbent section of the catheter into the portion of the catheter adjacent the diseased area to enable irradiating the diseased area. After completing the irradiation for the desired time, the radiation source may be moved back to within the absorbent section, or, more preferably, the wire is further retracted so that the radiation source becomes contained within another radiation absorbent section disposed proximally from the coiled distal end. The catheter and wire may then be withdrawn from the vessel or cavity. Alternatively, the entire catheter and wire may be drawn into a second, larger catheter, and withdrawn through or with the second catheter.

BRIEF DESCRIPTION OF THE DRAWINGS

Other objects and features of the present invention will be apparent to those skilled in the art, based on the following description, taken in combination with the accompanying drawings, wherein.

DETAILED DESCRIPTION OF THE PREFERRED EMBODIMENT

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims.

Figure 1A:
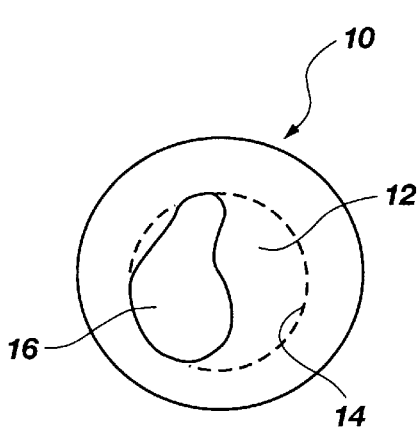
FIG. 1A shows a cross-sectional view of a blood vessel that is partially occluded by buildup on the inner surface thereof.
Figure 1B:
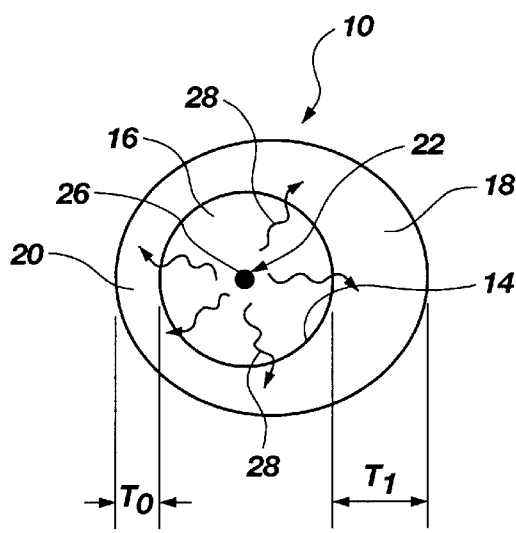
FIG. 1B shows a cross-sectional view of the blood vessel of FIG. 1A after balloon angioplasty, such that one side is substantially thicker than the other, and containing a prior art device for irradiating the inner surface thereof.

FIG. 1A shows a cross-sectional view of a blood vessel 10 that is partially occluded by buildup 12 on its inner surface 14. Such buildup or blockages may be created by a variety of causes, such as cholesterol, or excessive proliferation of smooth muscle cells on the inner wall 14 of the vessel 10. It will be apparent that this condition results in a substantial reduction of the cross-sectional area of the vessel lumen 16 and hence of blood flow through this section, which in the case of coronary arteries, for example, will result in damage to the coronary muscle, and may precipitate a heart attack or other serious coronary event. To remedy vessel blockages of this sort, balloon angioplasty is frequently used to widen the vessel to a proper diameter. FIG. 1B shows a cross-sectional view of the blood vessel 10 of FIG. 1A after balloon angioplasty, where the increase in inner vessel diameter is apparent.

However, while widening the vessel as needed, balloon angioplasty does not actually remove the blockage. As a result, the vessel will frequently be left with an excessively thick wall 18 on one side or another. This wall thickening is shown by comparison of the normal wall 20 having thickness $T_0$, with thickness $T_1$ of wall 18 as shown in FIG. 1B. Moreover, angioplasty does not remedy the underlying cause of the blockage, and after the procedure the vessel wall may continue to increase inwardly, eventually producing another blockage. For example, a lesion on the side 14 of the blood vessel 10 may precipitate smooth muscle cell proliferation, which will produce buildup toward the center of the vessel again.

To solve this problem, it has been found that exposing the inner vessel wall in the location where undesirable proliferation of smooth muscle cells is taking place to doses of radiation is effective to stop such undesirable cell proliferation. Also shown in FIG. 1B is a prior art device placed approximately in the center of the vessel for irradiating the inner surface thereof. This prior art device comprises a rod 24 or other elongate member which is impregnated with radioactive material 26 near its distal end, and is extended into a blood vessel or body cavity, approximately in the center thereof as shown. Radiation, symbolized by arrows 28, is emitted from the material 26 to irradiate the diseased portion 18 of the vessel 10. However, it will be apparent that with devices of this configuration, the entire wall of the vessel 10 will be exposed to approximately the same dose of radiation, including both diseased portions 18 and healthy portions 20. This raises several problems. First, the healthy tissue 20 is more likely to be damaged by the radiation exposure. Second, because the diseased tissue 18 is thicker and radiation decreases in intensity in proportion to the distance from the source, some of the tissue that most needs the exposure will receive less than some healthy tissues that need none. As a result, for the treatment to be effective, the total exposure intensity must be increased, resulting in more damaging exposure to healthy tissues.

Figure 2A:
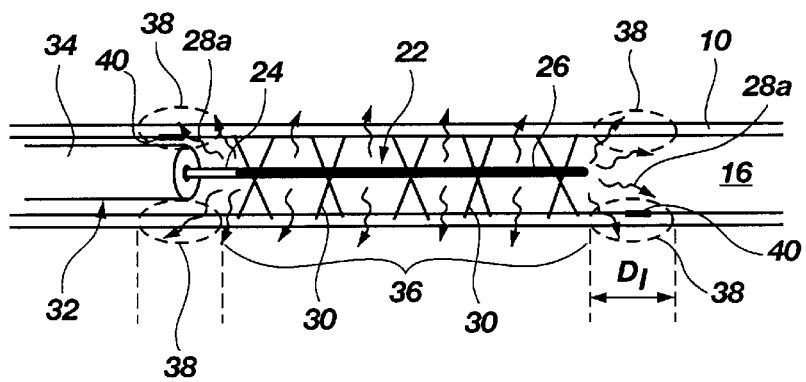
FIG. 2A shows a longitudinal cross-sectional view of a prior art radiation delivery device disposed within a blood vessel.

There are additional concerns with such prior art radiation exposure devices. FIG. 2A shows a longitudinal cross-sectional view of the prior art radiation delivery device 22 disposed within a blood vessel 10 having a plurality of stents 30 placed therein, such as from a previous procedure. The distal end 26 of the elongate rod is impregnated with radioactive material, and is frequently sheathed in a radiation absorbing tube during insertion into the patient, such as by a shielded portion 34 of the distal end of a delivery catheter 32. Upon reaching the target location 36 the radiation absorbing end 34 of the delivery catheter 32 is retracted, and the anatomy is exposed to radiation from the rod 26 for some predetermined length of time before the rod 26 is retracted back into the shielding end 34 of the catheter 32.

Figure 2B:
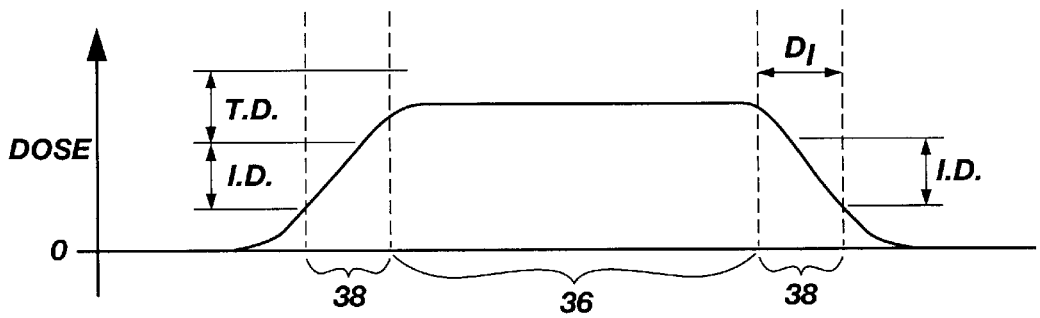
FIG. 2B shows a graph of the radiation dose provided by the radiation delivery device of FIG. 2A.

This prior art apparatus and method, however, presents several problems. First, radiation from the ends of the rod, symbolized by arrows 28a, will naturally irradiate portions of the vessel or cavity wall, designated generally at locations 38, beyond the target area 36, albeit with radiation levels which generally fall below the intended therapeutic level as one moves away from the radiation source. This radiation is sometimes called "edge effect" radiation. FIG. 2B shows a graph of the radiation dose provided by the prior art radiation delivery device of FIG. 2A as a function of the location along the length of the vessel wall, showing the radiation provided to the target area 36, and the edge effect radiation areas 38 at the extreme ends of the graph. To be effective against the diseased tissue, the radiation dose must be within a therapeutic dose window, designated T.D. in FIG. 2B.

Radiation in excess of this therapeutic dose will cause excessive damage to body tissues; radiation below the minimum therapeutic dose, outside the T.D. window, will not be effective to achieve the desired therapeutic results.

However, below the therapeutic dose window is an irritation dose window, designated I.D. in FIG. 2B. Irradiation of tissues with radiation doses below the I.D. window will have no effect. However, irradiation of tissues with radiation doses within the irritation dose range is responsible for many of the undesirable and dangerous side effects associated with radiation therapy. Such irritation radiation may cause lesions 40 in otherwise healthy tissue within the edge effect areas 38, thus prompting the growth of smooth muscle cells. Consequently, the edge effect radiation 28a may cause further disease in the very attempt to remedy it.

Figure 3:
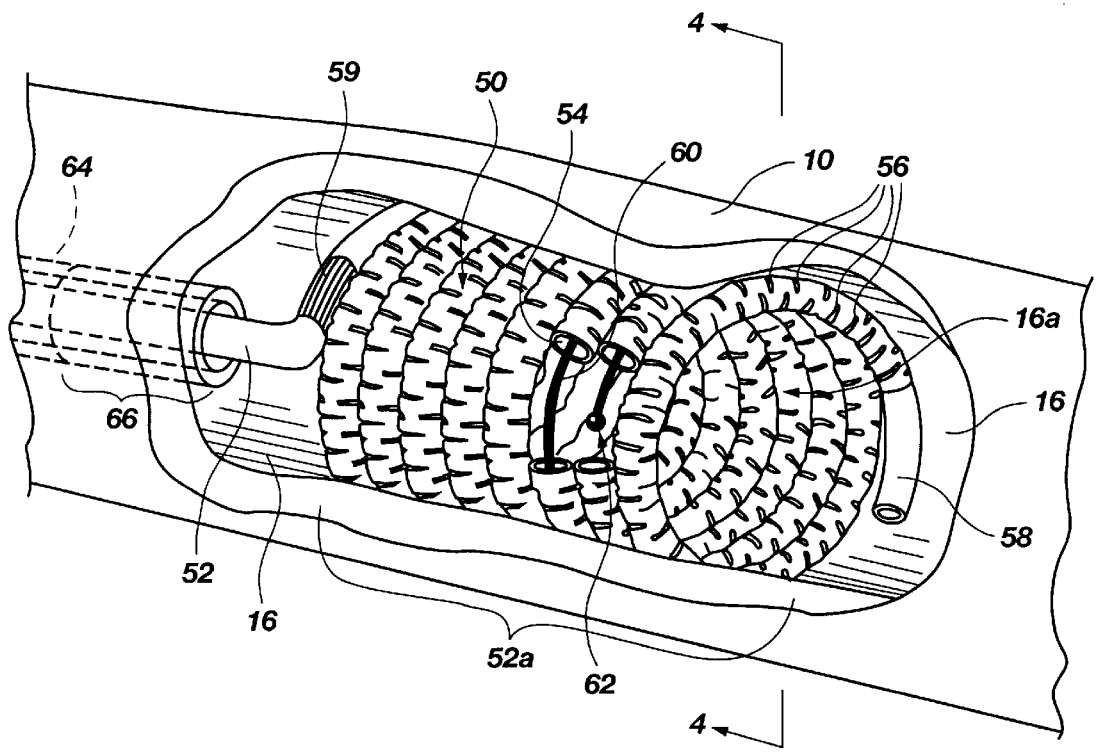
FIG. 3 shows a perspective, partially cut-away view of a radiation exposure device for vessels, body cavities and the like, made in accordance with the principles of the present invention.

To solve these and other problems, the inventors have developed a novel radiation delivery device 50, shown in FIG. 3, for exposing blood vessels, body cavities, and the like to more controllable radiation doses. This device, in various embodiments allows a radiation dose to be provided at a target location within a patient's anatomy, wherein the radiation dose may be both radially and longitudinally controlled. As shown in FIG. 3, the radiation delivery device 50 is shown inserted into a blood vessel 10, and generally comprises a catheter 52 having a single lumen 54. An end section 52a of the catheter 52 includes a plurality of cuts or grooves 56 positioned to provide flexibility. These cuts 56 may be formed only on the exterior of the coil only, or may be formed substantially on the exterior and interior of the coil, and are preferably staggered in their location on opposing sides of the catheter 52. The cuts 56 may extend either partially or completely through the thickness of the wall of the catheter 52, depending on the degree of radiation damping desired, and the desired degree of modification of the catheter flexibility and torsional stiffness, as will be explained below. In one embodiment, the cuts preferably have a depth approximately equal to 80% of the tube diameter.

The end section 52a of the catheter 52 is heat treated to produce a coil shape when unconstrained as shown, but is formed of a material which is flexible enough to be drawn into a second catheter 64 and straightened, and conversely, may be extended therefrom upon introduction into the patient's anatomy, to resume its coiled shape. Consistent with these requirements, the catheter 52 may be made of nitinol, stainless steel, or other suitable materials, including polymer materials. In the coiled shape, the coils of the end section 52a press against the walls of the vessel 10 at the target location as generally shown in FIG. 3, providing a central hollow 16a through which bodily fluids may freely flow. The cuts or grooves 56a and 56b are preferably made by saw cutting or grinding, such as with an abrasive cutting blade, but may also be made by chemical etching, EDM, or other mechanical or chemical process. See U.S. patent application Ser. No. 08/714,555, filed Sept. 16, 1996, which as now issued as U.S. Pat. No. 6,014,919.

Disposed on the distal end of the catheter 52 is a tubular section 58 which is generally absorbent of radioactive emissions. That is, tubular section 58 substantially blocks the escape of radioactive emissions from radiation sources located within it. The purpose of this will be discussed momentarily. To serve this purpose, the tubular end section 58 is preferably made of tungsten, platinum, or other material which is capable of blocking or absorbing radiation emissions, such as Beta or Gamma rays.

Shown disposed in the lumen 54 of the catheter 52 is a wire 60, at the distal end of which is located a radiation source 62. Radiation source 62 could be formed in a wide variety of shapes. In FIG. 3 it is shown as a ball, but it could also be formed as an elongate piece of any desired length, and may be housed in a plastic sheath or other container disposed on the distal and of the wire 60. In FIG. 3, the source 62 is shown disposed in a portion of the catheter 52 located adjacent one area of the side wall of the blood vessel 10. In this location, the radiation source 62 would be emitting radioactive emissions, with the largest dose affecting the area of the wall in closest proximity to the source. Advantageously, the radiation source 62 could be iridium 192, phosphorus 32, strontium 90, or other radiation source depending upon the treatment to be administered and the nature of the diseased area of the vessel 10. As is known to those skilled in the art, some of these radiation sources are beta emitters, and some are gamma emitters.

In use, the wire 60 would be threaded into the lumen 54 of the catheter 52 (under radio-protective conditions) until the radiation source 62 were positioned within the radiation absorbent section 58. There are then several alternative methods by which the catheter 52 may be extended to the target location. First, the catheter 52, with the wire disposed therein, could be threaded into the blood vessel 10 until the coil section 52 were disposed at the target location.

Alternatively, to facilitate ease of threading the catheter 52 into the patient, the coil section 52a could be uncoiled and threaded lengthwise into a slightly larger second catheter 64 which would prevent the coil section 52a from coiling. The second catheter 64 may be a typical venous catheter having a 0.014" lumen, or it may comprise some other size and shape configuration as desired. Consequently, the preferred outside diameter of the catheter 52 is 0.014", so as to coincide with the interior diameter of typical venous catheters. With this size of catheter 52, the cuts will preferably be from 0.004" to 0.012 inches deep, and be longitudinally spaced from 0.004" to 0.015" apart. The second catheter 64, with catheter 52 threaded therein, is then inserted into the desired blood vessel or body cavity until the target location is reached. The second catheter 64 will also shield some radiation from reaching tissues that are passed as the device is inserted into the patient, and may also be advantageously provided with a radiation absorptive section 66 at its distal end, which will shield even more radiation during insertion. As yet another alternative, the catheter 52 may be straightened and inserted into another catheter, similar to catheter 64, which is already in place, for example, if angioplasty has just been performed. The catheter 52 would be extended to the target location, and the previously placed catheter would be removed or retracted at least from the coil section 52a to allow the coil section to assume its coiled shape, expanded against the vessel 10 or body cavity walls.

Regardless of which method is followed, during the threading of the catheter 52 into the blood vessel or body cavity, the radiation source 62 is advantageously positioned in the radiation absorbent section 58 so that tissue past which the radiation source 62 moves is essentially protected from radioactivity. Additionally, the diameter of the catheter 52, and the second catheter 64 if provided, are chosen such that sufficient flow of bodily fluids is maintained through the vessel lumen 16 and the coil hollow 16a throughout the procedure. Progress of the catheter 52 or 64 into the anatomy may be tracked and monitored by any one of many methods well known in the art, such as x-ray fluoroscopy. Upon reaching the target location and expanding into its coiled shape, the wire 60 is partially withdrawn to move the radiation source 62 rearwardly in the catheter lumen 54 to the desired position against a side wall area to be irradiated. Such an area could be a diseased area infected with diseases such as smooth muscle cell proliferation or benign prostatic hyperplasia.

The configuration of the catheter 52 of this invention advantageously allows a user to control both the longitudinal and radial dose which is applied to the tissue. The longitudinal dose is controlled partly by the catheter 52 itself, which provides cuts 56a and 56b only on the outer and inner surfaces thereof relative to the coil lumen 16a. Thus, unlike the prior art device 22 shown in FIG. 2A, because no cuts are provided which face in the longitudinal directions, the material of the catheter itself significantly reduces the radiation dose which radiates in a forward or backward direction. Additionally, the longitudinal dose is controlled by the pitch of the coils 52a and the speed with which the radioactive portion 62 is drawn through the lumen 54. It will be apparent that these factors control the rate at which the radiation source 62 moves from the distal end of the coil to the proximal end thereof.

Figure 4:
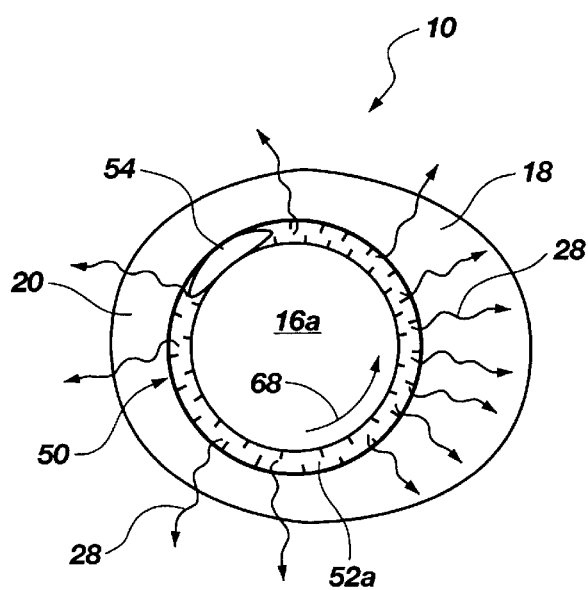
FIG. 4 shows a cross-sectional view of a blood vessel containing a radiation exposure device for vessels, body cavities and the like, made in accordance with the principles of the present invention.

FIG. 4 shows a cross-sectional view of the blood vessel 10 containing the radiation exposure device 50 of the present invention, taken along section A—A. In this view the central hollow 16a of the coil and the direct contact of the coil 52a with the vessel wall 10 are clearly shown. As the wire 60 is partially withdrawn from the catheter 52, it will negotiate a helical path as it passes through the catheter lumen 54, which in the cross-sectional view of FIG. 4 causes a generally circular path of motion for the radiation source, around the perimeter of the vessel as shown by arrow 68. It is this circular path that yields some of the great advantages of the present invention, as described in more detail below.

Figure 5A:
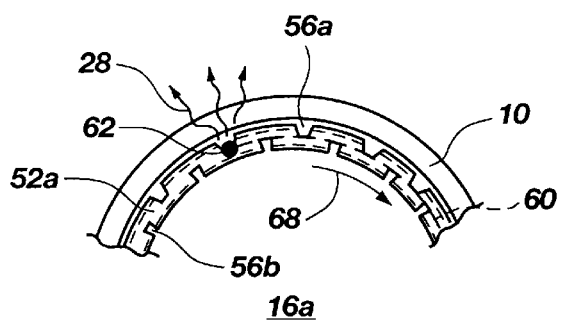
FIG. 5A shows a closeup cross-sectional view of a blood vessel containing the radiation exposure device of the present invention wherein the radiation source is located proximal to an exterior cut formed on the surface of the catheter.

FIG. 5A shows a closeup cross-sectional view of part of the blood vessel 10 of FIG. 4, containing the radiation exposure device 50 of the present invention. In this view the radiation source 62 is located proximal to an exterior cut 56a formed on the surface of the coiled end 52a of the catheter52. The radial dose of radiation is advantageously controlled by these cuts, and also by the rate at which the radiation source 62 is drawn past a specific location of the coil. In the preferred embodiment, the cuts 56 are formed to be in the range of 0.001" to 0.002" wide, but other widths may be used. It will be apparent that the depth and longitudinal spacing of the cuts will depend on the desired flexure and radiation resistance characteristics of the device, among other considerations.

When the coil is curved and disposed in the vessel as shown, it will be apparent that by virtue of this curvature, the cuts 56a disposed on the outer surface of the coil 52a will be stressed in an open configuration, thus providing a "window" for radiation, designated by arrows 28, to escape outwardly from the coil at each cut location. These cuts 56a may attain a width of 0.003" to 0.004" due to the bending of the catheter. However, because the cuts 56 are locationally staggered on opposite sides of the catheter, the inner surface of the catheter will provide no window at the location of an outer cut 56a, and will provide a reduced window at the location of the cuts 56b formed on the inner surface of the coil. This configuration will partially block radiation from passing through to the central hollow 16a of the coil, and thence into the opposing wall of the vessel or body cavity. The material of the catheter 52a on the opposing side of the coil will also serve to further shield the opposing vessel wall from this transverse radiation. The great advantage of this configuration is that it creates a more uniform "view factor" for the surface of the body cavity, which thereby provides a more uniform dose of radiation to the areas where it is needed, and a reduced dose to areas that do not need it.

Figure 5B:
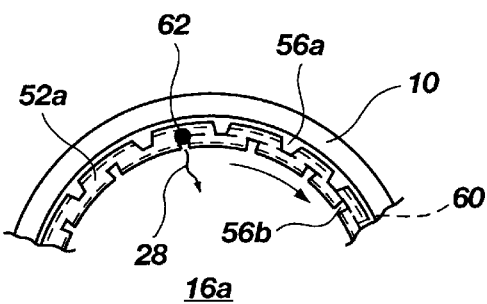
FIG. 5B shows a closeup cross-sectional view of a blood vessel containing the radiation exposure device of the present invention wherein the radiation source is located proximal to an interior cut formed on the surface of the catheter.

FIG. 5B shows a closeup cross-sectional view similar to that of FIG. 5A, except that the radiation source 62 is located proximal to an interior cut 56b formed on the surface of the catheter. As noted above, the curved configuration of the coil 52a causes these interior cuts to be mostly closed. Thus, while inner cuts 56b may be provided to increase the flexibility of the catheter, they will provide only a limited window for transverse radiation, shown by arrow 28, and the material of the catheter on the opposing side of the coil will serve to further block this transverse radiation. Thus when the radiation source 62 is located adjacent to a cut 56b formed on the inner surface of the coil 52a, the radial dispersion of radiation is still largely controlled.

Figure 5C:
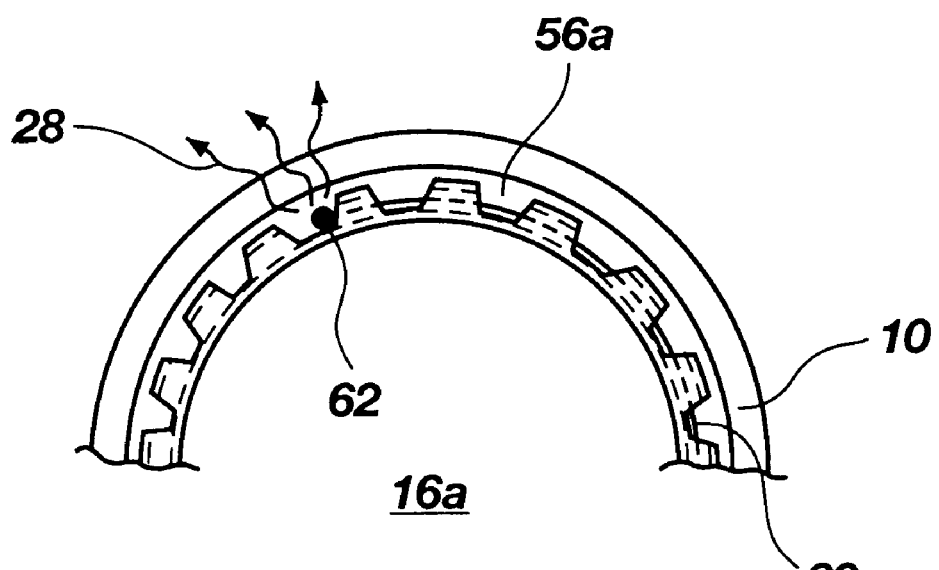
FIG. 5C shows a closeup cross-sectional view of a blood vessel containing an embodiment the radiation exposure device of the present invention wherein cuts are formed only on the outside surface of the coil.

For further control of radiation exposure, another alternative embodiment shown in FIG. 5C may be formed having cuts 56a only on the outside surface of the coil 52a. In this embodiment, the cuts 56a on the outside surface preferably extend to a depth approximately equal to 80% of the diameter of the catheter 52. This configuration significantly increases the flexibility of the distal end 52a of the catheter, and also provides a relative large, uniform window for radiation exposure. It also provides greater shielding on the inside of the coil, thus providing greater control of the exposure by blocking transverse radiation.

With the catheter 52 being coiled and having cuts as described, the radiation dosage may be very accurately controlled by adjusting the rate at which the radiation source 62 is retracted through the lumen 54. For example, the vessel 10 of FIG. 4 is shown with a thickened side wall 18. To prevent smooth muscle cell proliferation on the inner surface of the thickened portion 18 of the vessel wall, a therapeutic dose of radiation is required. However, because the opposing wall 20 is healthy, it is desirable not to expose that wall to even an irritation level of radiation. (See FIGS. 2A, 2B) This is easily accomplished with the present invention. Once the coil 52a is in place, the wire 60 may be retracted according to a predetermined speed profile so as to match the dose to the area in contact with the apparatus. For example, the speed of retraction may be varied such that in its circular path of motion about the helical coil, the radiation source 62 passes by healthy tissues 20 at a relatively high speed, such that the radiation dose thereto is minimal. However, the speed of retraction may be advantageously reduced when the radiation source 62 is adjacent the diseased wall portion 18, such that a larger dose is given thereto. The relative density of arrows 28 is intended to represent the variation in dosage at various locations around the perimeter of the vessel wall.

It will be apparent that retraction of the wire 60 through the tightly coiled catheter 52 will be resisted to some degree by friction between the wire and the inside wall of the catheter. This function will naturally limit the maximum length of the catheter coil 52a and the relative diameters of the wire 60 and the lumen of the catheter 52. However, friction may be advantageously reduced through the use of biocompatible lubricious coatings and lubricants well known in the art which will allow more easy movement of the wire 60 within the catheter 52. It will also be apparent that as with the catheter itself, the location of the radiation source 62 may be tracked by means of real-time x-ray imaging, x-ray fluoroscopy, angiography, or any other suitable tracking means known in the art. Such tracking may be perfomed relative to multiple axes, to provide very precise locational data.

Figure 6:
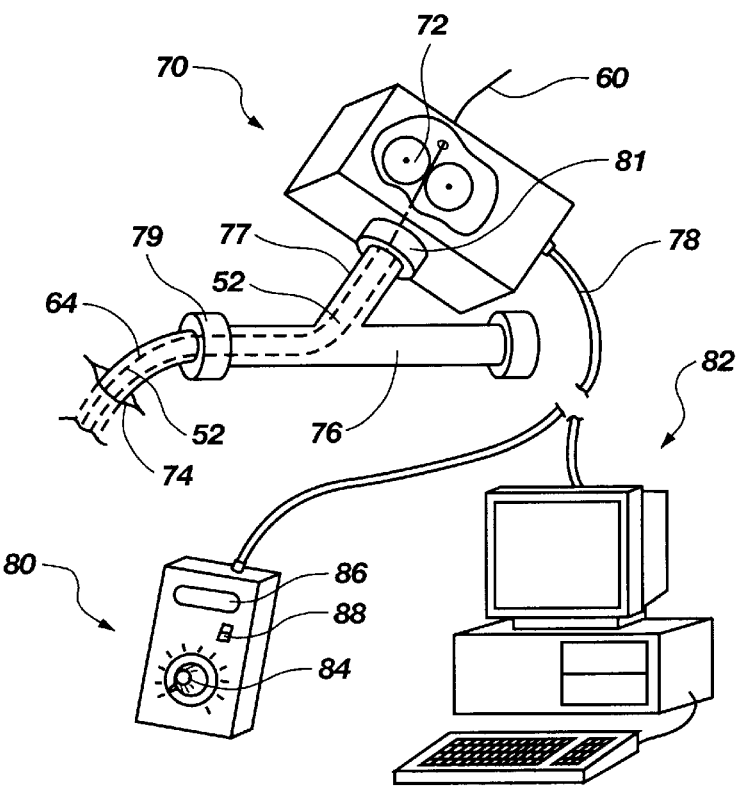
FIG. 6 shows a variable speed power retracting motor and its control apparatus for selectively retracting the flexible wire and radiation source through the catheter.

To assist in the variable speed retraction of the radiation source 62 through the catheter 52, the flexible wire 60 may be advantageously provided with a variable speed power retracting motor 70 and its control apparatus 80 or 82 as shown schematically in FIG. 6. FIG. 6 depicts the catheter 52 contained within a second catheter 64 extending from a small incision 74 in the patient, which is provided to introduce the apparatus. The catheters 64 and 52 are connected to the end of a rigid catheter insertion device 76 via a releasable connector 79. Such catheter insertion devices are well known in the art, and are routinely used in connection with angioplasty and other catheter-related or endoscopic procedures. In the embodiment as shown, the variable speed motor 70 is releasably connected via connector 81 to the proximal end of a branch 77 of the catheter insertion device 76. It will be apparent that devices of other configurations, such as without branches or with multiple branches, may be used without affecting the operation of the present invention.

The catheter 52 extends to the connection of the motor 70, and the wire 60 extends through the motor in such a manner as to allow retraction thereof The motor 70 comprises means 72 for gripping the proximal end of the wire 60 and pulling it out of the catheter 52. This means for gripping may comprise opposing wheels as shown, or other means such as a rotatable spool for winding the wire. The motor 70 is connected to a controller which controls its speed. In one relatively simple embodiment, the motor 70 is connected to a hand-held controller 80 which has a speed control knob 84, power switch 88, and control readout 86. In this embodiment, the user may manually control the speed of retraction of the radiation source, and monitor the retraction such as on an angiograph screen (not shown).

In the preferred embodiment, the controller comprises a computer 82, which is configured to cause the motor to retract the radiation source according to a preprogrammed exposure profile. The programmed exposure profile is designed to provide a uniform view factor to the affected tissue, and will allow for precise variation of the retraction speed, such that the portions of the anatomy most needing exposure receive a uniform therapeutic dose, but healthy portions receive much less—preferably less than an irritation dose. For example, the computer program may request information regarding the size and orientation of the target location, and the variation in the severity of the disease. Given these factors and the known diameter of the coil, the computer 82 calculates the speed variation required for optimal treatment, and automatically varies the speed of the motor 70 to cause the retraction speed to vary, such that the radiation source 62 will give precisely the proper exposure to each area of the vessel wall along its circular path—more exposure for more diseased locations, less exposure less diseased portions, and as little as possible for healthy tissue.

For embodiments of the invention having many turns of coil 52a, or having a small diameter coil, it may be desirable to provide means to more easily retract the wire 60 through the coil. There are several methods which could accomplish this. The wire 60, whether metal or polymer, could be lubricated with a suitably biocompatible lubricant. Additionally, the wire 60 could be vibrated as it is retracted to promote lubricity between the wire 60 and the lumen of the coil 52a. These vibrations could fall within the audible or ultrasonic ranges. Yet another method to promote lubricity could be to rotate or spin the wire 60 and radiation source 62 as it is retracted.

Upon completion of the desired dosage time, there are several alternative methods for removing and preparing to remove the device. To prepare for removal, it is generally desirable to again shield the radiation source 62. As one alternative, the radioactive source 62 could be moved forwardly in the catheter 52 (or the catheter 52 would be pulled rearwardly) until it were again positioned within the radiation absorbent section 58 at the distal tip. However, forward extension of the very thin wire 60 is very difficult. Alternatively, and more preferably, a second radioabsorbent section 59 could be provided at the proximal end of coil section 52a, (See FIGS. 3 & 6), and following irradiation of the tissue the wire 60 is further retracted until the radiation source 62 is positioned within radioabsorbent section 59. As a third alternative, the entire catheter 52 with the wire 60 and radiation source 62 contained therein could be retracted into the distal end of the second catheter 64. (See FIG. 3). To facilitate this method, the second catheter 64 is advantageously provided with a radiation absorbent section 66 on its distal end, as discussed above. It will be apparent that this radiation absorbent section 66 will need to have a length and location sufficient to ensure that the radiation source 62 will be shielded when the coil 52a is straightened and pulled into the second catheter 64. The catheter 52 may then be removed from the patient.

Following any of these preparatory methods, the second catheter 64 having the catheter 52 and wire 60 contained therein could be entirely removed from the patient. This may be accomplished by disconnecting the motor 70 from the wire 60, then disconnecting the catheter insertion device 76 from the second catheter 64 by means of connector 79, and removing the entire catheter assembly through the incision 74. Alternatively, if it is desired to leave the second catheter 64 in place for some other procedure, catheter 52 could be removed by disconnecting motor 70, and removing the radiation delivery catheter 52 with the wire 60 contained therein through the opening in connector 81.

This invention as described herein thus provides an accurate device and method for irradiating diseased tissues within the body, and allows control of both the longitudinal and radial exposure. It is to be understood that the above-described arrangements are only illustrative of the application of the principles of the present invention. Numerous modifications and alternative arrangements may be devised by those skilled in the art without departing from the spirit and scope of the present invention, and the appended claims are intended to cover such modifications and arrangements.

What is claimed is:

1. Apparatus for selectively radiating with radioactive emissions the inside surface of blood vessels, body cavities and the like of a patient, said apparatus comprising:

a resilient, elongate guide means configured for threading into and contacting the inside surface of a blood vessel, body cavity or the like, said guide means having a helical section shaped as a coil when unconstrained, yet configured to be straightenable for insertion into and movement through a catheter having a distal end, for discharge therefrom to re-assume a helical coil shape and occupy a target location adjacent said distal end, and having at least one lumen formed therein configured for guiding a radiation source in an arcuate path within the helical coil adjacent an interior wall of said blood vessel, body cavity or the like at the target location;

an elongate wire means slidably disposed within the lumen of the guide means, said wire means including a proximal end and a distal end; and a radiation source disposed near said distal end configured for exposing the tissue of the blood vessel, body cavity or the like to radioactive emissions.

2. Apparatus as in claim 1 further comprising:

a first catheter for containing and constraining said guide means in a straight configuration for insertion into the patient, said first catheter having a proximal end, a distal end, and a central lumen.

3. Apparatus as in claim 2 wherein said guide means comprises a second catheter having a central lumen, a proximal end, and a distal end, and said elongate wire means comprises a flexible wire disposed within the central lumen of said second catheter and extending from the proximal end to the distal end thereof, the distal end of said second catheter being configured to radially expand into a helical coil and contact the inside surface of the blood vessel, body cavity or the like at the target location when unconstrained, said helical coil having a central hollow whereby the radiation source will be caused to negotiate a helical path through said catheter when the flexible wire is slidably withdrawn from the distal end toward the proximal end of said catheter.

4. Apparatus as in claim 3 wherein said second catheter is formed of materials selected from the group consisting of nickel titanium alloy, stainless steel, and polymeric materials.

5. Apparatus as in claim 3 wherein the outside diameter of said second catheter is no greater than approximately 0.014 inches.

6. Apparatus as in claim 3 wherein the distal tip of said second catheter is absorbent to radioactive emissions from the radiation source, whereby radioactive emissions are substantially blocked from reaching adjacent tissue when the radiation source is positioned within said distal tip.

7. Apparatus as in claim 6 wherein said distal tip is made of a material selected from the group consisting of tungsten and platinum.

8. Apparatus as in claim 6 further comprising a radioactive emission absorbing section formed in the second catheter at a location toward the proximal end thereof relative to the expandable distal end thereof, whereby the radiation source may be retracted into said radioactive emission absorbing section, so as to substantially block radioactive emissions from reaching adjacent tissue.

9. Apparatus as in claim 8, wherein said radioactive emission absorbing section is made of a material selected from the group consisting of tungsten and platinum.

10. Apparatus as in claim 8 wherein said radioactive emission absorbing section comprises a hollow, generally cylindrical section formed in the catheter.

11. Apparatus as in claim 6 wherein the distal end of said first catheter comprises a radioactive emission absorbing section, whereby the first catheter having the radiation source contained therein may be retracted into the distal end of said first catheter, so as to substantially block radioactive emissions from reaching adjacent tissue.

12. Apparatus as in claim 1 wherein said radiation source comprises a source selected from the group consisting of beta radiation emitters and gamma radiation emitters.

13. Apparatus as in claim 12 wherein said beta radiation emitter is formed of a material selected from the group consisting of iridium 192, phosphorus 92, and strontium 90.

14. Apparatus as in claim 3 wherein said helical coil includes a plurality of cuts on the exterior surface thereof, formed to shape said portion into a coil, and provide openings to permit transmission of radiation outwardly from said coil, and to substantially inhibit transmission of radiation toward the interior of said coil.

15. Apparatus as in claim 14, wherein said cuts have a depth approximately equal to 80% of the diameter of said second catheter.

16. Apparatus as in claim 14, further comprising a plurality of cuts on the interior surface of said catheter, said interior cuts formed to shape said portion into a coil, and to generally close when said portion is in the coil configuration, to thereby inhibit transmission of radiation toward the interior of said coil.

17. Apparatus as in claim 4, further comprising:
a plurality of cuts formed on the exterior surface of said catheter so as to shape said distal end into a coil, and provide openings to permit transmission of radiation outwardly from said coil; and
a plurality of cuts formed on the interior surface of said catheter so as to shape said distal end into a coil, and to generally close when said distal end is in the coil configuration, to thereby inhibit transmission of radiation toward the interior of said coil.

18. Apparatus as in claim 17 wherein said cuts are formed by a method selected from the group consisting of cutting, grinding, etching, and EDM.

19. Apparatus as in claim 17 wherein the longitudinal locations of the plurality of cuts formed on the exterior surface and on the interior surface of said catheter are oppositely staggered.

20. Apparatus as in claim 17 wherein the plurality of cuts formed on the exterior surface and on the interior surface of said catheter extend from the outside surface to the central lumen thereof.

21. Apparatus as in claim 20 wherein the coiled section of said second catheter has a diameter approximately equal to 0.014 inches, and said cuts are from approximately 0.001 inches wide to approximately 0.002 inches wide when in an unstressed condition, are from approximately 0.004 inches to 0.012 inches deep, and are longitudinally spaced from approximately 0.004 inches to 0.015 inches apart.

22. Apparatus as in claim 3, further comprising power retraction means for mechanically retracting said flexible wire through the second catheter.

23. Apparatus as in claim 22, wherein said power retraction means further comprises speed adjustment means, whereby the speed of retraction of said flexible wire may be selectively adjusted.

24. An apparatus as in claim 1, further comprising cuts formed in the guide configured to facilitate straitening of the guide to be deployed through the catheter.

25. A device for irradiating with a desired radiation the walls of blood vessels, body cavities and the like of a patient, comprising:
a resilient elongate guide means having a central lumen, a proximal end, and a distal end, the distal end being configured to expand into a helical coil and contact the inside surface of the blood vessel, body cavity or the like at a target location when unconstrained, and to collapse and straighten when constrained for insertion into and movement through a catheter for discharge therefrom to expand and occupy the target location, said helical coil forming a central hollow when unconstrained for allowing bodily fluids to pass therethrough, said guide means being configured for guiding a radiation source contained within the lumen thereof through said helical coil;
a catheter for containing and constraining said guide means in a straight configuration for insertion into the patient;
a flexible wire slidably disposed within the central lumen of said guide means and extending from the proximal end to the distal end thereof, said flexible wire having a proximal end and a distal end, and having a radiation source disposed near the distal end whereby the radiation source will be caused to negotiate a helical path through said catheter when the flexible wire is slidably withdrawn from the distal end toward the proximal end of said catheter; and a radio-absorptive sleeve formed in the distal tip of said catheter, whereby radioactive emissions from the radiation source are substantially blocked from reaching adjacent tissue when the radiation source is positioned within said sleeve.

26. An apparatus for selectively radiating with radioactive emissions the inside surface of blood vessels, body cavities and the like of a patient, said apparatus comprising:

a catheter having a proximal end and a distal end, and configured for threading into a blood vessel, body cavity or the like, the distal end of said catheter being configured to be straightened for insertion into and movement through a catheter, and configured to expand into a coil so as to contact the inside surface of the blood vessel, body cavity or the like at a target location when unconstrained; and elongate wire means slidably disposed within the lumen of the catheter, said wire means including a proximal end and a distal end, and having a radiation source disposed near said distal end for exposing the tissue of the blood vessel, body cavity or the like to radioactive emissions when the wire means is slidably withdrawn from the distal end toward the proximal end of said catheter.

27. A method for irradiating the walls of a blood vessel, body cavity or the like with a desired radiation, said method comprising the steps of:

inserting an elongate hollow guide means into a blood vessel, body cavity or the like of a patient, such that the distal end of the guide means is located adjacent a target location, the guide means having a flexible wire slidably disposed within a central lumen thereof, said flexible wire having a radiation source disposed near its distal end, and enclosed in a radiation absorbtive section formed at the distal end of said guide means to shield tissue from radiation exposure;

expanding the distal end of the guide means into a helical coil so as to contact the inside surface of the blood vessel, body cavity or the like at the target location, said coil forming a central hollow for allowing bodily fluids to pass therethrough;

retracting the flexible wire through the guide means so as to draw the radiation source from the radiation absorbtive section at the distal end of the guide means, through the helical coil, toward the proximal end thereof, so as to irradiate the walls of the blood vessel, body cavity or the like; and withdrawing the guide means from the patient.

28. The method as in claim 27, wherein the step of retracting the wire so as to draw the radiation source through the coiled guide means further comprises the step of retracting the flexible wire at a variable speed, whereby the radiation source is located proximal to the portions of the anatomy requiring more radiation exposure for a longer time interval.

29. The method as in claim 27, further comprising the step of:

tracking the position of the distal end of said guide means while threading said apparatus into the anatomy of the patient; and tracking the position of said radiation source while retracting the flexible wire through the coiled guide means.

30. The method as in claim 27, wherein the step of withdrawing the apparatus from the patient further comprises the steps of:

retracting the radiation source into a radioactive emission absorbing section formed in the guide means at a location toward the proximal end thereof relative to the helically formed distal end thereof, to shield tissue from radiation exposure; and withdrawing the guide means from the patient with the radiation source contained within the radioactive emission absorbing section.

31. The method as in claim 27, wherein the step of inserting the guide means into the patient further comprises the steps of:

threading an elongate catheter into the blood vessel, body cavity or the like of the patient, such that the distal end of said catheter is advanced to a point near the target location; and inserting the guide means in a straightened condition into the lumen of said catheter and advancing said guide means so as to place its distal end adjacent to the target location.

32. The method as in claim 31 wherein the step of expanding the distal end of the guide means into a helical coil comprises the step of:

advancing said guide means beyond the distal end of said catheter, whereby the guide means may be unconstrained.

33. The method as in claim 31 wherein the step of expanding the distal end of the guide means into a helical coil comprises the step of:

retracting the distal end of said catheter from around the distal end of said guide means, whereby the guide means may be unconstrained.

34. The method as in claim 31 wherein the step of withdrawing the guide means from the patient further comprises the steps of:

retracting the radiation source into a radioactive emission absorbing section formed in the guide means at a location toward the proximal end thereof relative to the helically formed distal end thereof, to shield tissue from radiation exposure; and withdrawing the guide means from the catheter with the radiation source contained within said radioactive emission absorbing section.

35. The method as in claim 31 wherein the step of withdrawing the guide means from the patient further comprises the steps of:

retracting said guide means into a radioactive emission absorbing section formed in the distal end of said catheter such that the radiation source may be contained therein to shield tissue from radiation exposure; and withdrawing the catheter from the patient with the guide means contained therein.

36. The method as in claim 27, wherein the step of inserting the guide means into the patient further comprises the steps of:

inserting the guide means in a straightened condition into the lumen of a catheter such that the distal end of the guide means is contained within the distal end of the catheter;

threading the catheter into the blood vessel, body cavity or the like of the patient with the guide means disposed within the catheter during said threading, such that the distal end of the catheter and the enclosed guide means is advanced to a point near the target location.

37. The method as in claim 36 wherein the step of expanding the distal end of the guide means into a helical coil comprises the step of:

advancing said guide means beyond the distal end of said catheter, whereby the guide means may be unconstrained.

38. The method as in claim 36 wherein the step of expanding the distal end of the guide means into a helical coil comprises the step of:

retracting the distal end of said catheter from around the distal end of said guide means, whereby the guide means may be unconstrained.

39. The method as in claim 36 wherein the step of withdrawing the guide means from the patient further comprises the steps of:

retracting the radiation source into a radioactive emission absorbing section formed in the guide means at a location toward the proximal end thereof relative to the helically formed distal end thereof, to shield tissue from radiation exposure; and withdrawing the guide means from the catheter with the radiation source contained within said radioactive emission absorbing section.

40. The method as in claim 36 wherein the step of withdrawing the guide means from the patient further comprises the steps of:

retracting said guide means into a radioactive emission absorbing section formed in the distal end of said catheter such that the radiation source may be contained therein to shield tissue from radiation exposure; and withdrawing the catheter from the patient with the guide means contained therein.

\* \* \* \* \*